United States Patent
Schotes et al.

(10) Patent No.: US 12,410,138 B2
(45) Date of Patent: Sep. 9, 2025

(54) PROCESS COMPRISING THE USE OF NEW IRIDIUM CATALYSTS FOR ENANTIOSELECTIVE HYDROGENATION OF 4-SUBSTITUTED 1,2-DIHYDROQUINOLINES

(71) Applicant: Bayer Aktiengesellschaft, Leverkusen (DE)

(72) Inventors: Christoph Schotes, Duesseldorf (DE); Matthias Beller, Nienhagen (DE); Kathrin Junge, Rostock (DE); Weiping Liu, Shanghai (CN); Jacob Schneekoenig, Leipzig (DE); Thomas Leischner, Rostock (DE)

(73) Assignee: Bayer Aktiengesellschaft, Leverkusen (DE)

( * ) Notice: Subject to any disclaimer, the term of this patent is extended or adjusted under 35 U.S.C. 154(b) by 771 days.

(21) Appl. No.: 17/640,287

(22) PCT Filed: Sep. 22, 2020

(86) PCT No.: PCT/EP2020/076375
§ 371 (c)(1),
(2) Date: Mar. 3, 2022

(87) PCT Pub. No.: WO2021/058458
PCT Pub. Date: Apr. 1, 2021

(65) Prior Publication Data
US 2022/0324810 A1 Oct. 13, 2022

(30) Foreign Application Priority Data
Sep. 25, 2019 (EP) ...................... 19199636

(51) Int. Cl.
*C07D 215/08* (2006.01)
(52) U.S. Cl.
CPC .................. *C07D 215/08* (2013.01)
(58) Field of Classification Search
CPC .................................................. C07D 215/08
See application file for complete search history.

(56) References Cited

U.S. PATENT DOCUMENTS

| | | | |
|---|---|---|---|
| 9,796,678 B2 | 10/2017 | Takahashi et al. | |
| 10,349,656 B2 | 7/2019 | Dubost et al. | |
| 2017/0022162 A1 | 1/2017 | Takahashi et al. | |
| 2021/0009521 A1* | 1/2021 | Schotes ............... | B01J 31/2404 |

FOREIGN PATENT DOCUMENTS

| | | |
|---|---|---|
| CN | 106103413 A | 11/2016 |
| CN | 111902399 A | 11/2020 |
| DE | 11 2015 001290 T5 | 12/2016 |
| EP | 0 654 464 A1 | 5/1995 |
| EP | 3 103 789 A1 | 12/2016 |
| EP | 4112602 * | 3/2019 |
| WO | 2011/162397 A1 | 12/2011 |
| WO | 2012/084812 A1 | 6/2012 |
| WO | 2012171969 A1 | 12/2012 |
| WO | 2014096066 A1 | 6/2014 |
| WO | 2014096098 A1 | 6/2014 |
| WO | 2015/141564 A1 | 9/2015 |
| WO | 2015/197530 A2 | 12/2015 |
| WO | 2019/185541 A1 | 10/2019 |

OTHER PUBLICATIONS

Kaiser, Agnew Chem Int Ed, 2006, vol. 45, 5194-5197. (Year: 2006).*
International Search Report received in international application No. PCT/EP2020/076375, mailed Nov. 30, 2020, 3 pages.
Drury et al., "Synthesis of Versatile Chiral N,P Ligand Derived from Pyridine and Quinoline," Angewandte Chemie, International Edition, vol. 43, No. 1, Jan. 1, 2004, pp. 70-74.
Schneekonig et al., "Application of Crabtree/Pfaltz-Type Iridium Complexes for the Catalyzed Asymmetric Hydrogenation of an Agrochemical Building Blcok," Organic Process Research & Development, vol. 24, No. 3, Mar. 20, 2020, pp. 443-447.
Baeza et al., "Iridum-Catalyzed Asymmetric Hydrogenation of N-Protected Indoles," Chemistry—A European Journal, vol. 16, No. 7, Feb. 15, 2010, pp. 2036-2039.
Bernasconi, Maurizio et al., "Asymmetric Hydrogenation of Maleic Acid Diesters and Anhydrides**," Angew. Chem. Int. Ed. 2014, 53, 5385-5388.

(Continued)

*Primary Examiner* — D Margaret M Seaman

(57) ABSTRACT

New iridium catalysts for enantioselective hydrogenation of 4-substituted 1,2-dihydroquinolines The invention relates to a process for preparing optically active 4-substituted 1,2,3,4-tetra hydroquinolines (Ia, Ib) comprising enantioselective hydrogenation of the corresponding 4-substituted 1,2-dihydroquinolines in presence of a chiral iridium (P,N)-ligand catalyst.

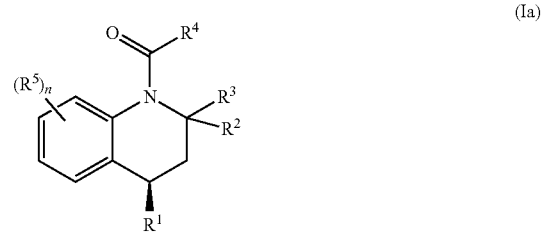

(Ia)

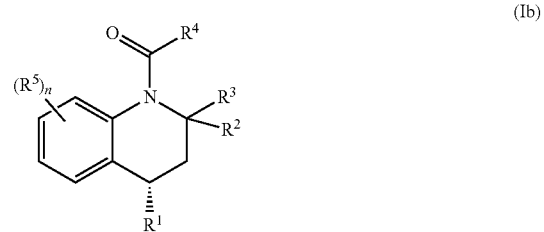

(Ib)

14 Claims, No Drawings

(56) References Cited

OTHER PUBLICATIONS

Mueller, Marc-Andre et al., "Recovery and Recycling of Chiral Iridium(N,P Ligand) Catalysts from Hydrogenation Reactions," Adv. Synth. Catal. 2018, 360, 1340-1345.

Roseblade, Stephen J. et al., "Study of chemoselective asymmetric hydrogenation of (1-bromo-1-alkenyl)boronic esters with iridiumeP/\N complexes," Tetrahedron 70, 2014, 2654-2660.

David H Woodmansee et al: "Chiral pyridyl phosphinites with large aryl substituents as efficient ligands for the asymmetric iridium-catalyzed hydrogenation of difficult substrates", Chemical Science, Royal Society of Chemistry, United Kingdom, vol. 1, May 1, 2010, pp. 72-78, XP002662994.

Kaiser et al., "Iridium Catalysts with Bicyclic Pyridine-Phosphinite Ligands: Asymmetric Hydrogenation of Olefins and Furan Derivatives", Angew. Chem. Int. Ed., 2006, vol. 45, pp. 5194-5197.

\* cited by examiner

PROCESS COMPRISING THE USE OF NEW IRIDIUM CATALYSTS FOR ENANTIOSELECTIVE HYDROGENATION OF 4-SUBSTITUTED 1,2-DIHYDROQUINOLINES

CROSS-REFERENCE TO RELATED APPLICATIONS

This application is the National Stage entry of International Application No. PCT/EP2020/076375, filed 22 Sep. 2020, which claims priority to European Patent Application No. 19199636.2, filed 25 Sep. 2019. Each of these applications is incorporated by reference in its entirety.

BACKGROUND

Field

The invention relates to a process for preparing optically active 4-substituted 1,2,3,4-tetrahydroquinolines comprising enantioselective hydrogenation of the corresponding 4-substituted 1,2-dihydroquinolines in presence of a chiral iridium (P,N)-ligand catalyst.

Description of Related Art

It is known from EP 0 654 464 that N-acetyl-tetrahydroquinolines can be converted to the corresponding 4-aminoindane derivatives via a rearrangement reaction. 4-aminoindane derivatives are important intermediates for preparing various N-indanyl heteroaryl carboxamides having fungicidal activity (EP 0 654 464, WO 2011/162397, WO 2012/084812, WO 2015/197530).

EP 3 103 789 discloses a method for optically resolving 1,1,3-trimethyl-4-aminoindane by converting the enantiomeric mixture into the diastereomeric salts of D-tartaric acid. (R)- and (S)-1,1,3-trimethyl-4-aminoindane are obtained after separation and basification of the diastereomeric salts. This reference also discloses a method for racemizing the undesired enantiomer, so that the whole method allows for converting the undesired enantiomer into the desired enantiomer via several process steps. (R)-1,1,3-trimethyl-4-aminoindane is an important intermediate for preparing the pyrazole carboxamide fungicide inpyrfluxam.

A method for preparing chiral intermediates of N-indanyl heteroaryl carboxamides via asymmetric synthesis is also known. WO 2015/141564 describes a process for preparing optically active 4-substituted 1,2,3,4-tetrahydroquinolines, which process comprises the hydrogenation of the corresponding 4-substituted 1,2-dihydroquinolines in presence of a transition metal catalyst having an optically active ligand. The asymmetric hydrogenation of the 4-substituted NH-dihydroquinolines proceeded with moderate conversion rates (up to 62.6%) and enantioselectivity (up to 71.3% ee), whereas N-acetyl-dihydroquinolines gave even poorer conversion (up to 14%) and enantioselectivity (up to 31% ee).

SUMMARY

In the light of the prior art described above, it is an object of the present invention to provide a process for preparing optically active 4-substituted 1,2,3,4-tetrahydroquinolines which process has advantages over the processes of the prior art. The process should allow the desired enantiomer to be prepared in high yield and high enantiomeric purity, with few process steps and few purification steps.

The object described above was achieved by a process for preparing a compound of the formula (Ta) or (Tb),

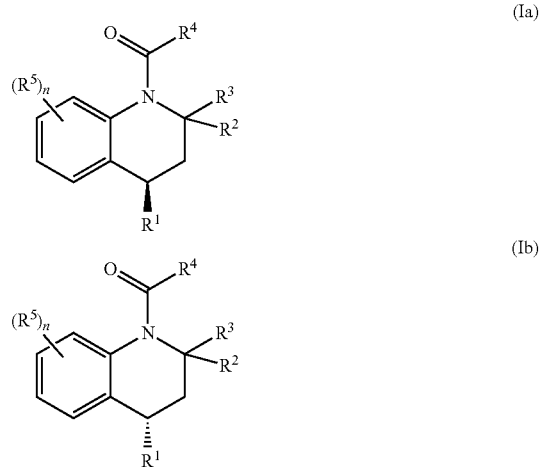

wherein
$R^1$ is selected from the group consisting of $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_6$-$C_{14}$-aryl, or $C_6$-$C_{14}$-aryl-$C_1$-$C_4$-alkyl,
wherein the $C_1$-$C_6$-alkyl, $C_3$-$C_6$-cycloalkyl and the $C_1$-$C_6$-alkoxy in the $C_1$-$C_6$-alkoxy-$C_1$-$C_6$-alkyl moiety, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and
wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy,
$R^2$ and $R^3$ are the same and are selected from the group consisting of hydrogen, $C_1$-$C_6$-alkyl, $C_1$-$C_6$-haloalkyl and $C_1$-$C_6$-alkoxy-$C_1$-$C_6$-alkyl,
or
$R^2$ and $R^3$ together with the carbon which they are bound to, form a $C_3$-$C_6$-cycloalkyl ring,
$R^4$ is hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_2$-$C_6$-alkenyloxy, 9-flurorenylmethyleneoxy, $C_6$-$C_{14}$-aryl, $C_6$-$C_{14}$-aryloxy, $C_6$-$C_{14}$-aryl-$C_1$-$C_4$-alkyloxy or $C_6$-$C_{14}$-aryl-$C_1$-$C_4$-alkyl,
wherein the $C_6$-$C_{14}$-aryl as such or as part of a composite substituent is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy,
n is 0, 1, 2, 3 or 4,
each substituent $R^5$, if present, is independently selected from the group consisting of halogen, $C_1$-$C_6$-alkyl, $C_1$-$C_6$-haloalkyl, $C_1$-$C_6$-alkoxy, hydroxyl, amino and —C(=O)—$C_1$-$C_6$-alkyl, comprising enantioselective hydrogenation of a compound of the formula (II)

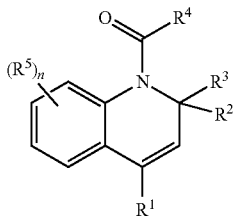

wherein the substituents $R^1$, $R^2$, $R^3$, $R^4$, $R^5$ and the integer n are each as defined for the compound of the formula (Ia) or (Ib),
in presence of a chiral iridium catalyst,
characterized in that the chiral iridium catalyst comprises a chiral ligand of the formula (IIIa) or (IIIb),

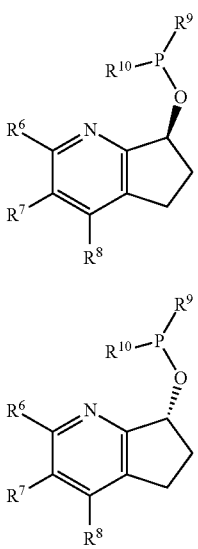

wherein
$R^6$ is a group of formula

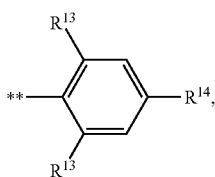

wherein
** denotes the bond to the 6,7-dihydro-5H-cyclopenta[b]pyridine moiety,
$R^{13}$ is hydrogen, methyl or ethyl,
$R^{14}$ is $C_1$-$C_6$-alkyl,
$R^7$ is hydrogen,
$R^8$ is $C_1$-$C_4$-alkyl or phenyl, wherein the phenyl is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^9$ and $R^{10}$ are independently from one another selected from the group consisting of $C_1$-$C_6$-alkyl, $C_3$-$C_5$-cycloalkyl, piperidinyl and pyridyl,
or
$R^9$ and $R^{10}$ together with the phosphorus atom which they are bound to form a group $G^1$ or $G^2$

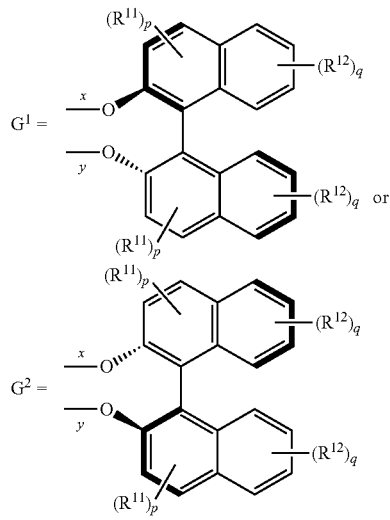

in which the bonds identified by "x" and "y" are both bound directly to the phosphorus atom,
p and q are independently from one another selected from 0, 1 and 2,
$R^{11}$ and $R^{12}$ are independently selected from $C_1$-$C_6$-alkyl and phenyl, which may be substituted by one to five substituents selected from the group consisting of halogen, $C_1$-$C_4$-alkyl, $C_1$-$C_4$-alkoxy and phenyl, which may be substituted by one or two $C_1$-$C_4$-alkyl substituents,
or
$R^9$ and $R^{10}$ together with the phosphorus atom which they are bound to form a group $G^3$

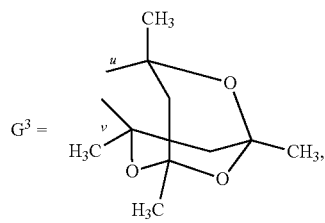 [SMILES: CC1(C)COC2(C)CC3(C1)C(C)(C)COC3(C)O2]

in which the bonds identified by "u" and "v" are both bound directly to the phosphorus atom.

DETAILED DESCRIPTION OF A PREFERRED EMBODIMENT

It has been found, surprisingly, that optically active 4-substituted 1,2,3,4-tetrahydroquinolines (Ia and Ib) can be prepared in high yields and excellent enantioselectivity by enantioselective hydrogenation of the corresponding 4-substituted 1,2-dihydroquinolines (II) in presence of a chiral iridium (P,N)-ligand catalyst.

Definitions

In the definitions of the symbols given in the above formulae, collective terms were used, which are generally representative of the following substituents:

Halogen: fluorine, chlorine, bromine or iodine, preferably fluorine, chlorine or bromine, and more preferably fluorine or chlorine.

Alkyl: saturated, straight-chain or branched hydrocarbyl substituents having 1 to 6, preferably 1 to 4 carbon atoms, for example (but not limited to) $C_1$-$C_6$-alkyl such as methyl, ethyl, propyl (n-propyl), 1-methylethyl (iso-propyl), butyl (n-butyl), 1-methylpropyl (sec-butyl), 2-methylpropyl (iso-butyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Particularly, said group is a $C_1$-$C_4$-alkyl group, e.g. a methyl, ethyl, propyl, 1-methylethyl (isopropyl), butyl, 1-methylpropyl (sec-butyl), 2-methylpropyl (iso-butyl) or 1,1-dimethylethyl (tert-butyl) group. This definition also applies to alkyl as part of a composite substituent, for example $C_3$-$C_6$-cycloalkyl-$C_1$-$C_4$-alkyl, $C_6$-$C_{14}$-aryl-$C_1$-$C_4$-alkyl etc., unless defined elsewhere.

Alkenyl: unsaturated, straight-chain or branched hydrocarbyl substituents having 2 to 6, preferably 2 to 4 carbon atoms and one double bond in any position, for example (but not limited to) $C_2$-$C_6$-alkenyl such as vinyl, allyl, (E)-2-methylvinyl, (Z)-2-methylvinyl, isopropenyl, homoallyl, (E)-but-2-enyl, (Z)-but-2-enyl, (E)-but-1-enyl, (Z)-but-1-enyl, 2-methylprop-2-enyl, 1-methylprop-2-enyl, 2-methylprop-1-enyl, (E)-1-methylprop-1-enyl, (Z)-1-methylprop-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, (E)-3,3-dimethylprop-1-enyl, (Z)-3,3-dimethylprop-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-1-enyl, (Z)-1-ethylbut-1-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, 1-(1,1-dimethylethyl)ethenyl, buta-1,3-dienyl, penta-1,4-dienyl, hexa-1,5-dienyl or methylhexadienyl. Particularly, said group is vinyl or allyl. This definition also applies to alkenyl as part of a composite substituent unless defined elsewhere.

Alkynyl: straight-chain or branched hydrocarbyl substituents having 2 to 8, preferably 2 to 6, and more preferably 2 to 4 carbon atoms and one triple bond in any position, for example (but not limited to) $C_2$-$C_6$-alkynyl, such as ethynyl, prop-1-ynyl, prop-2-ynyl, but-1-ynyl, but-2-ynyl, but-3-ynyl, 1-methylprop-2-ynyl, pent-1-ynyl, pent-2-ynyl, pent-3-ynyl, pent-4-ynyl, 2-methylbut-3-ynyl, 1-methylbut-3-ynyl, 1-methylbut-2-ynyl, 3-methylbut-1-ynyl, 1-ethylprop-2-ynyl, hex-1-ynyl, hex-2-ynyl, hex-3-ynyl, hex-4-ynyl, hex-5-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl. This definition also applies to alkynyl as part of a composite substituent unless defined elsewhere.

Alkylamino: monoalkylamino or dialkylamino, wherein monoalkylamino represents an amino radical having one alkyl residue with 1 to 4 carbon atoms attached to the nitrogen atom. Non-limiting examples include methylamino, ethylamino, n-propylamino, isopropylamino, n-butylamino and tert-butylamino. Wherein dialkylamino represents an amino radical having two independently selected alkyl residues with 1 to 4 carbon atoms each attached to the nitrogen atom. Non-limiting examples include N,N-dimethylamino, N,N-diethyl-amino, N,N-diisopropylamino, N-ethyl-N-methylamino, N-methyl-N-n-propylamino, N-isopropyl-N-n-propylamino and N-tert-butyl-N-methylamino.

Alkoxy: saturated, straight-chain or branched alkoxy substituents having 1 to 6, more preferably 1 to 4 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent unless defined elsewhere.

Cycloalkyl: mono- or polycyclic, saturated hydrocarbyl substituents having 3 to 12, preferably 3 to 8 and more preferably 3 to 6 carbon ring members, for example (but not limited to) cyclopropyl, cyclopentyl, cyclohexyl and adamantyl. This definition also applies to cycloalkyl as part of a composite substituent, for example $C_3$-$C_6$-cycloalkyl-$C_1$-$C_4$-alkyl, unless defined elsewhere.

Haloalkyl: straight-chain or branched alkyl substituents having 1 to 6, preferably 1 to 4 carbon atoms (as specified above), where some or all of the hydrogen atoms in these groups are replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy substituents having 1 to 6, preferably 1 to 4 carbon atoms (as specified above), where some or all of the hydrogen atoms in these groups are replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as part of a composite substituent, unless defined elsewhere.

Aryl: mono-, bi- or tricyclic aromatic or partially aromatic substituents having 6 to 14 carbon atoms, for example (but not limited to) phenyl, naphthyl, tetrahydronapthyl, indenyl and indanyl. The binding to the superordinate general structure can be carried out via any possible ring member of the aryl residue. Aryl is preferably selected from phenyl, 1-naphthyl, 2-naphthyl, 9-phenantryl und 9-antracenyl. Phenyl is particularly preferred.

The term "enantioselective" as used herein means that one of the two possible enantiomers of the hydrogenation product, namely the enantiomer of the formula (Ia) or the enantiomer of the formula (Ib), is preferably formed. The "enantiomeric excess" or "ee" indicates the degree of enantioselectivity:

$$\% \ ee = \frac{\text{major enantiomer (mol)} - \text{minor enantiomer (mol)}}{\text{major enantiomer (mol)} + \text{minor enantiomer (mol)}} \times 100\%$$

The major enantiomer can be controlled by the selection of the chiral ligand, for example by selecting the chiral ligand of the formula (IIIa) or the opposite enantiomer (the ligand of the formula (IIIb)).

The process according to the invention is used for preparing the compound of the formula (Ta) or (Tb), preferably (Ia).

Preferred are compounds of the formula (Ia) or (Ib), in particular (Ia), wherein the substituents are defined as follows:

$R^1$ is $C_1$-$C_6$-alkyl or $C_6$-$C_{14}$-aryl-$C_1$-$C_4$-alkyl,
  wherein $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^2$ and $R^3$ are the same and are selected from $C_1$-$C_4$-alkyl, $R^4$ is $C_1$-$C_4$-alkyl, $C_1$-$C_4$-haloalkyl, $C_1$-$C_4$-alkoxy, $C_1$-$C_4$-haloalkoxy, phenyl or benzyl, n is 0, 1 or 2, each substituent $R^5$, if present, is independently selected from the group consisting of halogen, $C_1$-$C_6$-alkyl and $C_1$-$C_6$-haloalkyl.

More preferred are compounds of the formula (Ia) or (Ib), in particular (Ia), wherein the substituents are defined as follows:

$R^1$ is $C_1$-$C_6$-alkyl $R^2$ and $R^3$ are the same and are selected from $C_1$-$C_4$-alkyl, or $R^2$ and $R^3$ together with the carbon which they are bound to, form a $C_3$-$C_6$-cycloalkyl ring, $R^4$ is $C_1$-$C_4$-alkyl, $C_1$-$C_4$-haloalkyl, phenyl or benzyl, n is 0, 1 or 2, each substituent $R^5$, if present, is independently selected from the group consisting of halogen and $C_1$-$C_6$-alkyl.

Even more preferred are compounds of the formula (Ia) or (Ib), in particular (Ia), wherein the substituents are defined as follows:

$R^1$ is methyl, ethyl or n-propyl, $R^2$ and $R^3$ are methyl, $R^4$ is $C_1$-$C_4$-alkyl, n is 0, 1 or 2, each substituent $R^5$, if present, is independently selected from the group consisting of halogen and $C_1$-$C_6$-alkyl.

Most preferred are compounds of the formula (Ia) or (Ib), in particular (Ia), wherein the substituents are defined as follows:

$R^1$ is methyl or n-propyl, $R^2$ and $R^3$ are methyl, $R^4$ is methyl, n is 0 or 1, substituent $R^5$, if present, is fluorine.

The process according to the invention comprises enantioselective hydrogenation of the compound of the formula (II). The substituents $R^1$, $R^2$, R, $R^4$, $R^5$ and the integer n in the compound of the formula (II) are each as defined for the compound of the formula (Ta) or (Tb).

The enantioselective hydrogenation of the compound of the formula (II) is conducted in presence of a chiral iridium catalyst comprising a chiral ligand of the formula (IIIa) or (IIIb).

In a preferred embodiment of the process according to the invention, the substituents of formulae (Ia), (Ib), (II), (IIIa), (IIIb) are defined as follows:

$R^1$ is $C_1$-$C_6$-alkyl or $C_6$-$C_{14}$-aryl-$C_1$-$C_4$-alkyl, wherein $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^2$ and $R^3$ are the same and are selected from $C_1$-$C_4$-alkyl, $R^4$ is $C_1$-$C_4$-alkyl, $C_1$-$C_4$-haloalkyl, $C_1$-$C_4$-alkoxy, $C_1$-$C_4$-haloalkoxy, phenyl or benzyl, n is 0, 1 or 2, each substituent $R^5$, if present, is independently selected from the group consisting of halogen, $C_1$-$C_6$-alkyl and $C_1$-$C_6$-haloalkyl, $R^6$ is a group of formula

**—⟨benzene with $R^{13}$ ortho, $R^{13}$ ortho, $R^{14}$ para⟩ wherein
** denotes the bond to the 6,7-dihydro-5H-cyclopenta[b]pyridine moiety,
$R^{13}$ is hydrogen, methyl or ethyl,
$R^{14}$ is $C_1$-$C_4$ alkyl,
$R^7$ is hydrogen,
$R^8$ is $C_1$-$C_4$ alkyl or phenyl,
  wherein the phenyl is unsubstituted or substituted by one to five $C_1$-$C_4$-alkyl substituents,
$R^9$ and $R^{10}$ are independently from one another selected from the group consisting of iso-propyl, tert-butyl, cyclopentyl, cyclohexyl and piperidin-1-yl.

In a more preferred embodiment of the process according to the invention, the substituents of formulae (Ia), (Ib), (II), (IIIa), (IIIb) are defined as follows:
$R^1$ is $C_1$-$C_6$-alkyl,
$R^2$ and $R^3$ are the same and are selected from $C_1$-$C_4$-alkyl,
$R^4$ is $C_1$-$C_4$-alkyl, $C_1$-$C_4$-haloalkyl, $C_1$-$C_4$-alkoxy, $C_1$-$C_4$-haloalkoxy, phenyl or benzyl,
n is 0, 1 or 2,
each substituent $R^5$, if present, is independently selected from the group consisting of halogen, $C_1$-$C_6$-alkyl and $C_1$-$C_6$-haloalkyl,
$R^6$ is a group of formula

**—⟨benzene with $R^{13}$ ortho, $R^{13}$ ortho, $R^{14}$ para⟩ wherein
** denotes the bond to the 6,7-dihydro-5H-cyclopenta[b]pyridine moiety,
$R^{13}$ is ethyl,
$R^{14}$ is methyl,
$R^7$ is hydrogen,
$R^8$ is methyl,
$R^9$ and $R^{10}$ are independently from one another selected from the group consisting of cyclohexyl and piperidin-1-yl.

In the most preferred embodiment of the process according to the invention, the substituents of formulae (Ia), (Ib), (II), (IIIa), (IIIb), are defined as follows:
$R^1$ is $C_1$-$C_4$-alkyl,
$R^2$ and $R^3$ are methyl,
$R^4$ is $C_1$-$C_4$-alkyl,
n is 0 or 1,
$R^5$ if present, is fluorine,
$R^6$ is 2,6-diethyl-4-methylphenyl,
$R^7$ is hydrogen,
$R^8$ is methyl,
$R^9$ and $R^{10}$ are both cyclohexyl.

Depending on whether compound (Ia) or (Ib) is the desired product, the ligand of the formula (IIIa) or (IIIb) is selected.

Preferred are ligands of the formulae (IIIa) and (IIIb), wherein the substituents are defined as follows:
$R^6$ 2,6-diethyl-4-methylphenyl,
$R^7$ is hydrogen,
$R^8$ is methyl,
$R^9$ and $R^{10}$ are both cyclohexyl.

Preferably, the chiral iridium catalyst is selected from the group consisting of [IrL*(COD)]Y and [IrL*(nbd)]Y, wherein
L* is the chiral ligand of the formulas (IIIa) and (IIIb),
COD represents 1,5-cyclooctadiene,
nbd represents norbornadiene, and
Y is a non-coordinating anion selected from the group consisting of $[B(R^{18})_4]^-$, $PF_6^-$ and $[Al\{OC(CF_3)_3\}_4]^-$ of formula (VII)

(VII)

⟨structure of aluminum alkoxide anion with nine $CF_3$ groups around central Al⟩ wherein $R^{18}$ is selected from fluorine and phenyl, which is unsubstituted or substituted with one to five substituents selected from $C_1$-$C_4$-alkyl, $C_1$-$C_4$-haloalkyl and halogen.

More preferred are chiral iridium catalysts of the formulae [IrL*(COD)]Y and [IrL*(nbd)]Y, wherein Y is $[Al\{OC(CF_3)3\}_4]^-$ of formula (VII) or $[B(R^{18})_4]^-$, wherein $R^{18}$ is phenyl, which is unsubstituted or substituted with one to five substituents selected from fluorine and trifluoromethyl.

Even more preferred are chiral iridium catalysts of the general formulae (Va) and (Vb)

(Va)

⟨structure of Ir complex with COD, P($R^9$)($R^{10}$), pyridine ring with $R^6$, $R^7$, $R^8$ substituents, and [Y]$^-$ counterion⟩

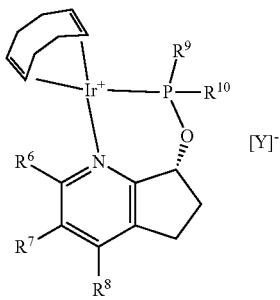

(Vb)

wherein
R⁶ 2,6-diethyl-4-methylphenyl,
R⁷ is hydrogen,
R⁸ is methyl,
R⁹ and R¹⁰ are both cyclohexyl
Y is a non-coordinating anion selected from the group consisting of $[B(R^{18})_4]^-$ and $[Al\{OC(CF_3)_3\}_4]^-$ of formula (VII),
wherein R¹⁸ is 3,5-bis(trifluoromethyl)phenyl.

Most preferred are chiral iridium catalysts of the general formula (Va)

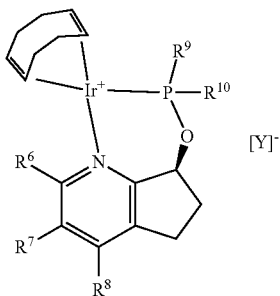

(Va)

wherein
R⁶ is 2,4,6-trimethylphenyl,
R⁷ is hydrogen,
R⁸ is methyl,
R⁹ and R¹⁰ are both cyclohexyl,
Y is $[Al\{OC(CF_3)3\}_4]^-$ of formula (VII).

The amount of iridium catalyst used is preferably within the range of from 0.001 mol % to 5 mol %, more preferably 0.001 mol % to 4 mol %, most preferably 0.002 mol % to 3 mol %, in particular 0.005 mol % to 1.0 mol %, based on the amount of the compound of the formula (II).

The chiral iridium catalyst may be prepared by methods known in the art from an iridium (I) catalyst precursor, such as $[Ir(COD)Cl]_2$, the chiral ligand of the formula (IIIa) or (IIIb) and an alkali salt of the non-coordinating anion (S. Kaiser et al., Angew. Chem. Int. Ed. 2006, 45, 5194-5197; W. J. Drury III et al., Angew. Chem. Int. Ed. 2004, 43, 70-74).

The process according to the invention comprises enantioselective hydrogenation of the compound of the formula (II).

Preferably, the hydrogenation is conducted using hydrogen gas at a pressure of from 1 to 300 bar, preferably 3 to 200 bar, most preferably 20 to 150 bar.

The hydrogenation is preferably conducted at a temperature within the range of from 20° C. to 130° C., more preferably 30° C. to 100° C.

Suitable solvents are halogenated alcohols such as 2,2,2,-trifluoroethanol, hexafluoroisopropanol (1,1,1,3,3,3-hexafluoro-2-propanol) and tetrafluoropropanol (2,2,3,3-tetrafluoro-1-propanol), halogenated hydrocarbons, such as chlorobenzene, dichlorobenzene, dichloromethane, chloroform, tetrachloromethane, dichloroethane and trichloroethane, aromatic hydrocarbons such as benzene, toluene and xylene, ethers such as diethyl ether, diisopropyl ether, methyl tert-butyl ether, methyl tert-amyl ether, dioxane, tetrahydrofuran, 1,2-dimethoxyethane, 1,2-diethoxyethane and anisole, and esters such as ethyl acetate, isopropyl acetate, and mixtures thereof.

Preferred solvents are selected from the group consisting of 2,2,2,-trifluoroethanol, hexafluoroisopropanol, 1,2-dichloroethane, tetrafluoropropanol, 1,4-dioxane, isopropyl acetate, toluene, and mixtures thereof.

More preferred solvents are selected from the group consisting of 2,2,2,-trifluoroethanol, hexafluoroisopropanol, 1,2-dichloroethane, tetrafluoropropanol, and mixtures thereof.

Especially preferred are 2,2,2,-trifluoroethanol and hexafluoroisopropanol.

Most preferred is hexafluoroisopropanol.

The process according to the invention may optionally be conducted in the presence of an additive, which is selected from the group consisting of Bronsted acids and Lewis acids.

In a preferred embodiment of the process according to the invention, the additive is selected from the group consisting of hexafluorophosphoric acid, acetic acid, trifluoromethylsulfonic acid, water, pentafluorophenol, 3,5-bis(trifluoromethyl)phenol, tetrafluoroboric acid, tetrafluoroboric acid diethylether complex, nafion, amberlyst, 1,1,1,3,3,3-hexafluoro-2-(trifluoromethyl)propan-2-ol, triphenylborane, tris[3,5-bis(trifluoro-methyl)phenyl]borane, tris(2,3,4,5,6-pentafluorophenyl)borane, borane tetrahydrofurane complex, boric acid, aluminum (III) trifluoromethanesulfonate, zinc (II) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof.

Suitable complexes of boron trifluoride are complexes of boron trifluoride with organic solvents, such as dialkyl ethers or alcohols, and complexes of boron trifluoride with organic acids, such as carboxylic acids. Preferred boron trifluoride complexes are selected from the group consisting of boron trifluoride-diethylether complex, boron trifluoride acetic acid complex and boron trifluoride n-propanol complex.

In a more preferred embodiment of the process according to the invention, the additive is selected from the group consisting of hexafluorophosphoric acid, pentafluorophenol, 3,5-bis(trifluoromethyl)phenol, tetra-fluoroboric acid diethylether complex, triphenylborane, tris[3,5-bis(trifluoromethyl)phenyl]borane, tris(2,3,4,5,6-pentafluorophenyl) borane, aluminum (III) trifluoromethanesulfonate, scandium (III) trifluoro-methanesulfonate, aluminum (III) fluoride, titanium (IV) isopropoxide, trimethyl aluminum, boron trifluoride, complexes of boron trifluoride, and mixtures thereof, wherein the complexes of boron trifluoride are preferably selected from the group consisting of boron trifluoride-diethylether complex, boron trifluoride acetic acid complex and boron trifluoride n-propanol complex.

In an even more preferred embodiment of the process according to the invention, the additive is selected from the group consisting of hexafluorophosphoric acid, pentafluorophenol, 3,5-bis(trifluoromethyl)phenol, tri-phenylborane, tris[3,5-bis(trifluoromethyl)phenyl]borane, tris(2,3,4,5,6-pentafluorophenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof, wherein the complexes of boron trifluoride are preferably selected from the group consisting of boron trifluoride-diethylether complex, boron trifluoride acetic acid complex and boron trifluoride n-propanol complex.

In the most preferred embodiment of the process according to the invention, the additive is selected from the group consisting Most preferred are aluminum (III) trifluoromethanesulfonate, scandium (III) trifluoro-methanesulfonate, tris(2,3,4,5,6-pentafluorophenyl)borane, hexafluorophosphoric acid, boron trifluoride and complexes of boron trifluoride, wherein the complexes of boron trifluoride are preferably selected from the group consisting of boron trifluoride diethylether complex, boron trifluoride acetic acid complex and boron trifluoride n-propanol complex.

The amount of additive selected from the group consisting of Bronsted acids and Lewis acids used is preferably within the range of from 0.1 mol % to 10 mol %, more preferably 0.2 mol % to 5 mol %, most preferably 0.3 mol % to 2 mol %, in particular 0.4 mol % to 1 mol %, based on the amount of the compound of the formula (II).

Abbreviations and Acronyms

| a/a | |
|---|---|
| Ac | Acetyl |
| BARF | Tetrakis[3,5-bis(trifluoromethyl)phenyl]-borate |
| CgPBr | 8-bromo-1,3,5,7-tetramethyl-2,4,6-trioxa-8-phosphatricyclo[3.3.1.13,7]decane |
| c-hexane | cyclohexane |
| ClP-(S-BINOL) | (S)-1,1'-Binaphthyl-2,2'-diyl phosphorochloridate |
| Cy | Cyclohexyl |
| DCM | dichloromethane |
| GC-FID | Gas chromatography - Flame ionization detector |
| HPLC | High performance liquid chromatography |
| Et | Ethyl |
| Me | Methyl |
| n-BuLi | n-Butyllithium |
| PTFE | Polytetrafluoroethylene |
| RT | Room temperature |
| SFC | Supercritical fluid chromatography |
| THF | tetrahydrofurane |
| Tf | Trifluoromethylsulfonyl |
| TFE | 2,2,2-Trifluoroethanol |

Preparation of Iridium Catalysts

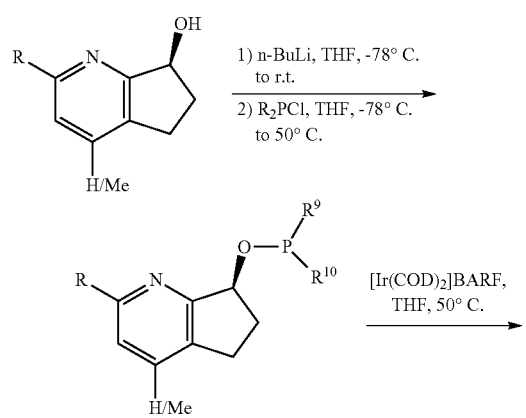

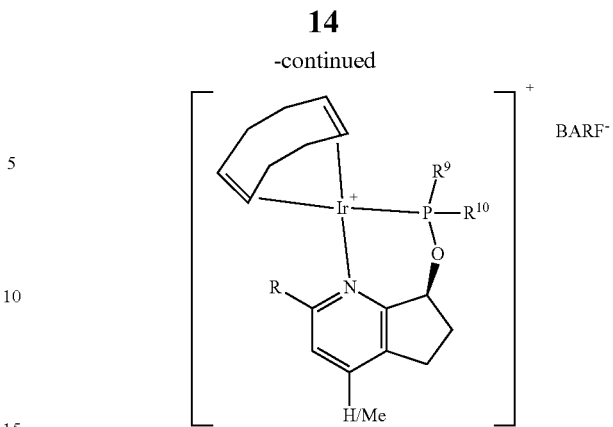

The ligand precursors (enantiomerically enriched secondary alcohols) were prepared according to known literature procedures like to the method disclosed in S. Kaiser et al., Angew. Chem. Int. Ed. 2006, 45, 5194-5197 or in D. H. Woodmansee Chem. Sci 2010, 1, 72. The ligands and iridium complexes were prepared by a modified procedure based on the same literature precedents:

Standard Procedures

Procedure of ligand synthesis (under Ar): A solution of alcohol precursor in THF (0.25 mmol, in 5.0 mL THF) was cooled to −78° C. and n-BuLi (0.1 mL of a 2.5 M n-BuLi solution in hexane; 0.25 mmol; 1 eq.) was added dropwise to the continuously stirred solution. After completion of the addition the solution was allowed to warm to room temperature and was stirred at this temperature for further 30 min. The solution was cooled to −78° C. again and $R^9R^{10}PCl$ (0.25 mmol, 1 eq.) was added to the continuously stirred solution. The mixture was allowed to warm to room temperature and subsequently heated to 50° C. and kept at this temperature overnight. The theoretical yield of ligand was calculated using $^{31}P$-NMR and the ligand was used for the next step without further purification.

Procedure of complexation (under Ar): To the crude ligand solution was added [Ir(COD)$_2$]BARF (BARF=Tetrakis[3,5-bis(trifluoromethyl)phenyl]-borate) (as a solid, 1 eq. based on the theoretical yield). The resulting mixture was heated to 50° C. and kept at this temperature for 3 h.

Work-up (under air): After cooling to room temperature the reaction solution is rotary evaporated onto silica, loaded onto a column of silica. Side components were eluted using pentane/diethylether and the desired complexes subsequently with DCM. The solvent was then evaporated under reduced pressure.

The following specified catalysts were synthesized and characterized:

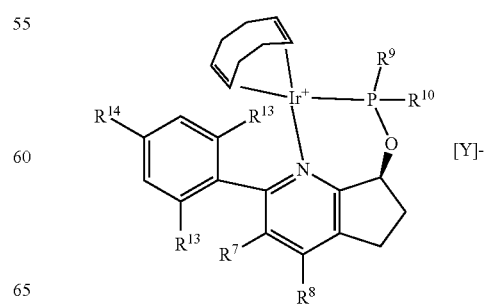

TABLE 1

| Catalyst | $R^8$ | $R^9$, $R^{10}$ | $R^7$ | $R^{13}$ | $R^{14}$ | $[Y]^-$ |
|---|---|---|---|---|---|---|
| Va-1 | methyl | Cyclohexyl | H | Et | Me | Tetrakis(3,5-bis(trifluoromethyl)phenyl)borate |
| Va-2 | methyl | cyclohexyl | H | Et | Me | $[\text{Al}\{\text{OC}(\text{CF}_3)_3\}_4]^-$ of formula (VII) |
| Va-3 | phenyl | cyclohexyl | H | Et | Me | Tetrakis(3,5-bis(trifluoromethyl)phenyl)borate |
| Va-4 | methyl | S-BINOL*-yl | H | Et | Me | Tetrakis(3,5-bis(trifluoromethyl)phenyl)borate |
| Va-5 | methyl | piperidin-1-yl | H | Et | Me | Tetrakis(3,5-bis(trifluoromethyl)phenyl)borate |
| Va-6 | methyl | cyclohexyl | H | Me | tBu | $PF_6^-$ |
| Va-7 | methyl | Cg-Phos** | H | Me | H | Tetrakis(3,5-bis(trifluoromethyl)phenyl)borate |
| Va-8 | methyl | tBu, 2-pyridyl | H | Me | H | Tetrakis(3,5-bis(trifluoromethyl)phenyl)borate |
| Va-9 | methyl | cyclohexyl | H | Me | H | $[\text{Al}\{\text{OC}(\text{CF}_3)_3\}_4]^-$ of formula (VII) |
| Va-10 | methyl | cyclohexyl | H | Me | Me | Tetrakis(3,5-bis(trifluoromethyl)phenyl)borate |
| Va-11 | methyl | cyclohexyl | H | Me | tBu | Tetrakis(3,5-bis(trifluoromethyl)phenyl)borate |
| Va-12 | methyl | cyclohexyl | H | Me | H | Tetrakis(3,5-bis(trifluoromethyl)phenyl)borate |
| Va-13 | H | phenyl | H | H | H | Tetrakis(3,5-bis(trifluoromethyl)phenyl)borate |

BINOL* (S)-(—)-1,1'-Binaphthalene-2,2'-diol,

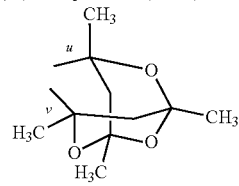

Cg-Phos **

Va-1

The reaction was performed according to the above described standard procedure. The complex could be isolated as an orange solid (282 mg; 76% based on [Ir(COD)$_2$]BARF).

$^1$H-NMR (300 MHz, CD$_2$Cl$_2$): δ (ppm)=7.73 (s, 8H), 7.56 (s, 4H), 7.23 (s, 1H), 7.14 (s, 1H), 7.00 (s, 1H), 5.62 (dd, J=8.0, 5.6 Hz, 1H), 5.46-5.39 (m, 1H), 4.32 (dd, J=7.4, 3.4 Hz, 1H), 3.36-3.27 (m, 1H), 3.19-3.06 (m, 2H), 3.01-2.91 (m, 2H), 2.80 (dq, J=14.9, 7.4 Hz, 1H), 2.59-2.43 (m, 2H), 2.43-2.15 (m, 7H), 2.15-0.83 (m, 36H), 0.66-0.48 (m, 1H). $^{31}$P-NMR (122 MHz, CD$_2$Cl$_2$) δ (ppm)=119.00. $^{19}$F-NMR (282 MHz, CD$_2$Cl$_2$) δ (ppm)=−62.87. HR-MS (ESI) m/z calcd for C40H58NOPIr [M]$^+$ 792.3880 found 792.3903.

Va-2

A solution of the respective alcohol precursor in THF (0.25 mmol, in 5.0 mL THF) was cooled to −78° C. and n-BuLi (0.1 mL of a 2.5 M n-BuLi solution in hexane; 0.25 mmol; 1 eq.) was added dropwise to the continuously stirred solution. After completion of the addition the solution was allowed to warm to room temperature and was stirred at this temperature for further 30 min. The solution was cooled to −78° C. again and Cy$_2$PCl (0.25 mmol, 1 eq.) was added to the continuously stirred solution. The mixture was allowed to warm to room temperature and subsequently heated to 50° C. and kept at this temperature overnight. After the reaction was cooled down to RT, THF was removed and dried in vacuum, [Ir(COD)Cl]$_2$ (0.125 mmol) and DCM (5.0 mL) were added to the tube, stirred at 50° C. for 2 h. Then Li{Al[OC(CF$_3$)$_3$]$_4$}(0.275 mmol) was added to the reaction mixture and stirred at RT for overnight. The reaction solution is rotary evaporated onto silica, loaded onto a column of silica prepared with DCM chromatographed with n-heptane/DCM: 1/1 to afford the orange solid (140 mg, 32%).

$^1$H-NMR (300 MHz, CD$_2$Cl$_2$) δ=7.27 (s, 1H), 7.18 (s, 1H), 7.04 (s, 1H), 5.66 (dt, J=8.0, 3.8 Hz, 1H), 5.50-5.44 (m, 1H), 4.40-4.31 (m, 1H), 3.46-3.26 (m, 1H), 3.25-2.91 (m, 4H), 2.91-2.77 (m, 1H), 2.57-2.52 (m, 2H), 2.50-2.20 (m, 7H), 2.19-1.78 (m, 13H), 1.70-1.53 (m, 5H), 1.49-1.02 (m, 18H), 0.62 (s, 1H). $^{31}$P-NMR (122 MHz, CD$_2$Cl$_2$) δ=119.02. $^{19}$F-NMR (282 MHz, CD$_2$Cl$_2$) δ=−75.74. HR-MS (ESI) m/z calcd for C$_{45}$H$_{60}$NOPIr [M]$^+$ 792.3880 found 792.3903.

Va-3

The reaction was performed according to the above described standard procedure. The complex could be isolated as an orange solid (162 mg; 42% based on [Ir(COD)$_2$]BARF).

$^1$H-NMR (300 MHz, CD$_2$Cl$_2$) δ=7.80-7.65 (m, 8H), 7.65-7.41 (m, 10H), 7.17 (s, 1H), 7.04 (s, 1H), 5.70-5.65 (m, 1H), 5.53-5.47 (m, 1H), 4.42-4.35 (m, 1H), 3.43-3.32 (m, 2H), 3.27-3.09 (m, 2H), 3.09-2.93 (m, 1H), 2.86 (dq, J=14.8, 7.4 Hz, 1H), 2.55-2.48 (m, 2H), 2.38 (s, 3H), 2.27-1.46 (m, 19H), 1.46-0.74 (m, 18H), 0.69-0.52 (m, 1H). $^{31}$P-NMR (122 MHz, CD$_2$Cl$_2$) δ=119.07. $^{19}$F-NMR (282 MHz, CD$_2$Cl$_2$) δ=−62.87. HR-MS (ESI) m/z calcd for C$_{45}$H$_{60}$NOPIr [M]$^+$ 854.4036 found 854.4073.

Va-4

The reaction was performed using ClP-(S)-BINOL (0.25 mmol, freshly prepared) and [Ir(COD)$_2$]BARF (287 mg, 0.225 mmol) according to the above described standard procedure. The complex could be isolated as an orange solid (104 mg) after three times column chromatography using Heptane/DCM: 1/1. There are still four peaks showing in $^{31}$P NMR, the main peak is in 117.72 ppm (around 80% purity). The HRMS shows that the desired complex is present.

$^{31}$P-NMR (122 MHz, CD$_2$Cl$_2$) δ=120.36, 117.72, 114.61, 92.27. $^{19}$F-NMR (282 MHz, CD$_2$Cl$_2$) δ=−62.85. HR-MS (ESI) m/z calcd for C$_{48}$H$_{48}$NO$_3$PIr [M]$^+$ 910.2996 found 910.3026.

Va-5

The reaction was performed according to the above described standard procedure, using 1,1'-(chlorophosphanediyl)dipiperidine (0.25 mmol, freshly prepared). The complex could be isolated as a red solid (149 mg). There are 6 peaks showing in $^{31}$P NMR, the main peak is in 102.35 and 98.87 ppm (2:3). The HRMS shows that the desired complex is present.

$^{31}$P-NMR (122 MHz, CD$_2$Cl$_2$) δ=102.35, 101.96, 101.40, 98.87, 98.46, 98.35. $^{19}$F-NMR (282 MHz, CD$_2$Cl$_2$) δ=−62.87. HR-MS (ESI) m/z calcd for C$_{39}$H$_{58}$N$_3$OPIr [M]$^+$ 808.3941 found 808.3958.

Va-6

A solution of the respective alcohol precursor in THF (0.25 mmol, in 5.0 mL THF) was cooled to −78° C. and n-BuLi (0.1 mL of a 2.5 M n-BuLi solution in hexane; 0.25 mmol; 1 eq.) was added dropwise to the continuously stirred solution. After completion of the addition the solution was allowed to warm to room temperature and was stirred at this temperature for further 30 min. The solution was cooled to −78° C. again and Cy$_2$PCl (0.25 mmol, 1 eq.) was added to the continuously stirred solution. The mixture was allowed to warm to room temperature and subsequently heated to 50° C. and kept at this temperature overnight. After the reaction was cooled down to RT, THF was removed and dried in vacuum, [Ir(COD)Cl]$_2$ (0.125 mmol) and DCM (5.0 mL) were added to the tube, stirred at 50° C. for 2 h. Then KPF$_6$ (0.25 mmol) was added to the reaction mixture and stirred at RT for overnight. The reaction solution is rotary evaporated onto silica, loaded onto a column of silica prepared with DCM chromatographed with EtOAc/DCM: 1/10 to afford the orange solid after two times column chromatography (130 mg, 55%).

$^1$H-NMR (300 MHz, CD$_2$Cl$_2$) δ=7.37-7.02 (m, 3H), 5.74-5.56 (m, 1H), 5.52-5.46 (m, 1H), 4.47-4.30 (m, 1H), 3.45-3.21 (m, 1H), 3.19-2.92 (m, 3H), 2.66 (s, 3H), 2.63-2.48 (m, 2H), 2.44 (s, 3H), 2.40-2.19 (m, 2H), 2.16-1.70 (m, 15H), 1.68-1.46 (m, 6H), 1.41-1.28 (m, 13H), 1.18-0.95 (m, 5H), 0.71-0.58 (m, 1H). $^{31}$P-NMR (122 MHz, CD$_2$Cl$_2$) δ=118.42, −127.01, −132.85, −138.70, −144.55, −150.39, −156.24, −162.09. $^{19}$F-NMR (376 MHz, CD$_2$Cl$_2$) δ=−72.64, −74.52. HR-MS (ESI) m/z calcd for C$_{41}$H$_{60}$NOPIr [M]$^+$ 806.4036 found 806.4061.

Va-7

The reaction was performed according to the above described standard procedure, using CgPBr (0.25 mmol, freshly prepared). The complex could be isolated as an orange solid (120 mg). There are two peaks showing in $^{31}$P NMR. The HRMS shows that the desired complex is present.

$^{31}$P-NMR (122 MHz, CD$_2$Cl$_2$) δ=89.41, 83.71. $^{19}$F-NMR (282 MHz, CD$_2$Cl$_2$) δ=−62.86. HR-MS (ESI) m/z calcd for C$_{35}$H$_{46}$NO$_4$PIr [M]$^+$ 768.2788 found 768.2816.

Va-8

The reaction was performed according to the above described standard procedure, using 2-(tert-butylchlorophosphaneyl)pyridine (0.25 mmol). The complex could be isolated as a red solid (196 mg). There are 2 peaks showing in $^{31}$P NMR at 107.59 and 102.97 ppm (1:1.4). The HRMS shows that the desired complex is present. $^{31}$P-NMR (122 MHz, CD$_2$Cl$_2$) δ=107.59, 102.97. $^{19}$F-NMR (282 MHz, CD$_2$Cl$_2$) δ=−62.83. HR-MS (ESI) m/z calcd for C$_{34}$H$_{43}$N$_2$OPIr [M]$^+$ 719.2737 found 719.2757.

Va-9

A solution of the respective alcohol precursor in THF (0.25 mmol, in 5.0 mL THF) was cooled to −78° C. and n-BuLi (0.1 mL of a 2.5 M n-BuLi solution in hexane; 0.25 mmol; 1 eq.) was added dropwise to the continuously stirred solution. After completion of the addition the solution was allowed to warm to room temperature and was stirred at this temperature for further 30 min. The solution was cooled to −78° C. again and Cy$_2$PCl (0.25 mmol, 1 eq.) was added to the continuously stirred solution. The mixture was allowed to warm to room temperature and subsequently heated to 50° C. and kept at this temperature overnight. After the reaction was cooled down to RT, THF was removed and dried in vacuum, [Ir(COD)Cl]$_2$ (0.125 mmol) and DCM (5.0 mL) were added to the tube, stirred at 50° C. for 2 h. Then Li{Al[OC(CF$_3$)$_3$]$_4$}(0.275 mmol) was added to the reaction mixture and stirred at RT for overnight. The reaction solution is rotary evaporated onto silica, loaded onto a column of silica prepared with DCM chromatographed with n-heptane/DCM: 1/1 to afford the orange solid (122 mg, 28%).

$^1$H-NMR (300 MHz, CD$_2$Cl$_2$) δ=7.40-7.12 (m, 4H), 5.67-5.63 (m, 1H), 5.50-5.42 (m, 1H), 4.43-4.36 (m, 1H), 3.39-3.30 (m, 1H), 3.25-2.90 (m, 3H), 2.67 (s, 3H), 2.60-2.42 (m, 4H), 2.42-2.18 (m, 2H), 2.13-1.99 (m, 5H), 1.96-1.71 (m, 9H), 1.65-1.52 (m, 5H), 1.45-1.01 (m, 12H), 0.69-0.53 (m, 1H). $^{31}$P-NMR (121 MHz, CD$_2$Cl$_2$) δ=118.81. $^{19}$F-NMR (282 MHz, CD$_2$Cl$_2$) δ=−75.74. HR-MS (ESI) m/z calcd for C$_{37}$H$_{52}$NOPIr [M]$^+$ 750.3416 found 750.3420.

Va-10 The reaction was performed according to the described procedure using 287 mg of [Ir(COD)$_2$]BARF (0.225 mmol). The complex could be isolated as an orange solid (148 mg; 40% based on [Ir(COD)$_2$]BARF).

$^1$H-NMR (300 MHz, CD$_2$Cl$_2$): δ (ppm)=7.91-7.46 (m, 12H), 7.21 (s, 1H), 7.09 (s, 1H), 6.94 (s, 1H), 5.67-5.63 (m, 1H), 5.46-5.41 (m, 1H), 4.38-4.36 (m, 1H), 3.36-3.32 (m, 1H), 3.19-2.85 (m, 3H), 2.64 (s, 3H), 2.53-2.46 (m, 2H), 2.41 (s, 3H), 2.35 (s, 3H), 2.31-2.18 (m, 2H), 2.19-1.83 (m, 14H), 1.68-1.54 (m, 6H), 1.38-1.20 (m, 5H), 1.14-0.97 (m, 5H), 0.68-0.56 (m, 1H). $^{31}$P-NMR (122 MHz, CD$_2$Cl$_2$) δ=118.64. $^{19}$F-NMR (282 MHz, CD$_2$Cl$_2$) δ=−62.87. HR-MS (ESI) m/z calcd for C$_{38}$H$_{54}$NOPIr [M]$^+$ 764.3572 found 764.3577.

Va-11

The reaction was performed according to the above described procedure. The complex could be isolated as an orange solid (274 mg; 73% based on [Ir(COD)$_2$]BARF).

$^1$H-NMR (300 MHz, CD$_2$Cl$_2$): δ (ppm)=7.79-7.66 (m, 8H), 7.56 (s, 4H), 7.29 (s, 1H), 7.23 (s, 1H), 7.13 (s, 1H), 5.65 (td, J=5.9, 2.2 Hz, 1H), 5.46-5.40 (m, 1H), 4.42-4.36 (m, 1H), 3.38-3.30 (m, 1H), 3.19-2.86 (m, 3H), 2.65 (s, 3H), 2.59-2.44 (m, 2H), 2.42 (s, 3H), 2.38-1.54 (m, 20H), 1.46-0.98 (m, 21H), 0.70-0.58 (m, 1H). $^{31}$P-NMR (122 MHz, CD$_2$Cl$_2$) δ (ppm)=118.67. $^{19}$F-NMR (282 MHz, CD$_2$Cl$_2$) δ (ppm)=−62.86. HR-MS (ESI) m/z calcd for C$_{41}$H$_{60}$NOPIr [M]$^+$ 806.4042 found 806.4053.

Va-12

The reaction was performed according to the above described procedure using 287 mg of [Ir(COD)$_2$]BARF (0.225 mmol). The complex could be isolated as an orange solid (298 mg; 82% based on [Ir(COD)$_2$]BARF).

$^1$H-NMR (300 MHz, CD$_2$Cl$_2$): δ (ppm)=7.80-7.52 (m, 12H), 7.42-7.19 (m, 3H), 7.12 (d, J=7.5 Hz, 1H), 5.65 (td, J=5.6, 2.6 Hz, 1H), 5.48-5.42 (m, 1H), 4.43-4.37 (m, 1H), 3.38-3.30 (m, 1H), 3.21-2.89 (m, 3H), 2.67 (s, 3H), 2.58-2.45 (m, 2H), 2.42 (s, 3H), 2.38-2.16 (m, 2H), 2.13-2.05 (m, 3H), 2.02-1.89 (m, 4H), 1.84 (s, 3H), 1.81-1.72 (m, 2H), 1.64-1.49 (m, 3H), 1.39-1.19 (m, 8H), 1.12-0.99 (m, 4H), 0.68-0.56 (m, 1H). $^{31}$P-NMR (122 MHz, CD$_2$Cl$_2$) δ=118.80.

$^{19}$F-NMR (282 MHz, CD$_2$Cl$_2$) δ=−62.88. HR-MS (ESI) m/z calcd for C$_{37}$H$_{52}$NOPIr [M]$^+$ 750.3416 found 750.3420.

EXAMPLES

Reactions were performed in metal autoclaves. Reaction mixtures were analyzed without workup via HPLC (Chiralpak IC column, 95/5 heptane/ethanol, 1 mL/min) or SFC (OZ-H column, 2.5% MeOH in supercritical CO$_2$, 3 mL/min) chromatography.

Examples 1-12

The Ir-complex (catalyst loading given) and 0.64 g 1-(2,2,4-trimethyl-1-quinolyl)ethanone (3 mmol) were placed in an 8-mL autoclave vial containing a PTFE-coated stirring bar. The autoclave vial was closed using a screw cap with septum and flushed with argon (10 min). Hexafluoroisopropanol (HFIP, 4 mL) was added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the vial was taken out of the autoclave and the reactions outcome was determined by GC-FID analysis (deluted with EtOH) and the enantiomeric excess by HPLC analysis. Typical values are given.

TABLE 2

| Example | Catalyst | Reaction time (h) | catalyst loading (mol %) | Conversion GC (% a/a) | Enantiomeric excess (% ee) |
|---|---|---|---|---|---|
| 1 | Va-6 | 3 | 0.02 | 78.8 | 98.8 |
| 2 | Va-11 | 3 | 0.02 | 85.2 | 98.8 |
| 3 | Va-4 | 3 | 0.02 | <1 | — |
| 4 | Va-5 | 3 | 0.02 | 58 | n.d. |
| 5 | Va-7 | 3 | 0.02 | <1 | — |
| 6 | Va-8 | 3 | 0.02 | 2 | — |
| 7 | Va-3 | 3 | 0.02 | 37.5 | n.d. |
| 8 | Va-1 | 16 | 0.025 | 98.2 | 96.2 |
| 9 | Va-1 | 6 | 0.03 | 94.9 | n.d. |
| 10 | Va-2 | 6 | 0.03 | 96.1 | n.d. |
| 11 | Va-9 | 16 | 0.03 | 81.3 | n.d. |
| 12 | Va-12 | 16 | 0.03 | 79.4 | n.d. |

Examples 13-18

The Ir-complex (catalyst loading given) and 2.56 g 1-(2,2,4-trimethyl-1-quinolyl)ethanone (12 mmol) were placed in an 25-mL autoclave. The autoclave was flushed with argon (10 min). Hexafluoroisopropanol (HFIP, 16 mL) was added to the autoclave. The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the reactions outcome was determined by GC-FID analysis (deluted with EtOH) and the enantiomeric excess by HPLC analysis.

TABLE 3

| Example | Catalyst | Reaction time (h) | catalyst loading (mol %) | Conversion GC (% a/a) |
|---|---|---|---|---|
| 13 | Va-10 | 17 | 0.01 | 82.5 |
| 14 | Va-10 | 40 | 0.01 | 93.9 |
| 15 | Va-1 | 17 | 0.01 | 93.1 |
| 16 | Va-1 | 40 | 0.01 | 98.0 |
| 17 | Va-1 | 6 | 0.01 | 50.8 |
| 18 | Va-2 | 6 | 0.01 | 53.4 |

Examples 19-48

The Ir-complex Va-1 (catalyst loading given) and 0.64 g 1-(2,2,4-trimethyl-1-quinolyl)ethanone (3 mmol, purified with heptane: water wash+crystallization) were placed in an 8-mL autoclave vial containing a PTFE-coated stirring bar. The autoclave vial was closed using a screw cap with septum and flushed with argon (10 mi). Hexafluoroisopropanol (HFIP, 4 mL) and additive (loading given) were added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the vial was taken out of the autoclave and the reactions outcome was determined by GC-FID analysis (deluted with EtOH) and the enantiomeric excess by HPLC analysis. Typical values are given.

TABLE 4

| Example | Additive (mol %) | Reaction time (h) | catalyst loading (mol %) | Conversion GC (% a/a) | Enantiomeric excess (% ee) |
|---|---|---|---|---|---|
| 19 | — | 16 | 0.02 | 95.3 | n.d. |
| 20 | — | 21 | 0.02 | 95.5 | n.d. |
| 21 | — | 3 | 0.02 | 55.2 | n.d. |
| 22 | — | 16 | 0.03 | 97.6 | n.d. |
| 23 | Pentafluorophenol (1) | 16 | 0.02 | 97.2 | n.d. |
| 24 | 1,2,2,6,6-Pentamethylpiperidin (1) | 16 | 0.02 | 67.1 | n.d. |
| 25 | Nonafluoro-tert-butyl alcohol (1) | 16 | 0.03 | 96.3 | n.d. |
| 26 | Nonafluoro-tert-butyl alcohol (5) | 16 | 0.03 | 97.5 | n.d. |
| 27 | 3,5-bis-trifluorophenol (1) | 16 | 0.02 | 95.7 | n.d. |

TABLE 4-continued

| Example | Additive (mol %) | Reaction time (h) | catalyst loading (mol %) | Conversion GC (% a/a) | Enantiomeric excess (% ee) |
|---|---|---|---|---|---|
| 28 | AcOH (1) | 16 | 0.02 | 96 | n.d. |
| 29 | AcOH (5) | 3 | 0.02 | 66.5 | n.d. |
| 30 | AcOH (10) | 3 | 0.02 | 63.7 | n.d. |
| 31 | AcOH (20) | 3 | 0.02 | 54.2 | n.d. |
| 32 | $HPF_6$ (1) | 3 | 0.02 | >99 | n.d. |
| 33 | $HBF_4$*$OEt_2$ (1) | 16 | 0.02 | 90.5 | n.d. |
| 34 | TfOH (1) | 16 | 0.02 | 76.9 | n.d. |
| 35 | $Sc(OTf)_3$ (1) | 3 | 0.02 | >99 | 99 |
| 36 | $BF_3$*$OEt_2$ (1) | 3 | 0.02 | 98.9 | 98 |
| 37 | $BH_3$*THF (1) | 3 | 0.02 | 69.8 | n.d. |
| 38 | $BF_3$*AcOH (1) | 3 | 0.02 | >99 | n.d. |
| 39 | $BF_3$*n-PrOH (1) | 3 | 0.02 | >99 | n.d. |
| 40 | $Al(OTf)_3$ (1) | 3 | 0.02 | >99 | n.d. |
| 41 | $AlF_3$ (1) | 3 | 0.02 | 65.9 | n.d. |
| 42 | $AlMe_3$ (1) | 3 | 0.02 | 91.1 | n.d. |
| 43 | $Ti(O^iPr)_4$ (1) | 3 | 0.02 | 90.7 | n.d. |
| 44 | $BPh_3$ (1) | 3 | 0.02 | 85.4 | n.d. |
| 45 | $B(C_6F_5)_3$ (1) | 3 | 0.02 | >99 | 97.6 |
| 46 | $B(C_6F_5)_3$ (0.5) | 3 | 0.02 | 97.3 | n.d. |
| 47 | $B(C_6F_5)_3$ (0.1) | 3 | 0.02 | 63.3 | n.d. |
| 48 | $B(OH)_3$ (1) | 3 | 0.02 | 72.7 | n.d. |

Examples 49-54

The Jr-complex Va-1 (catalyst loading given) and 1-(2,2,4-trimethyl-1-quinolyl)ethanone (amount given; purified with heptane: water wash+crystallization) were placed in an 25-mL autoclave. The autoclave was flushed with argon (10 min). Hexafluoroisopropanol (1.33 mL per mmol of 1-(2,2,4-trimethyl-1-quinolyl)ethenone)) and additive (loading given) were added to the autoclave. The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the reactions outcome was determined by GC-FID analysis (deluted with EtOH) and the enantiomeric excess by HPLC analysis.

purified with heptane: water wash+crystallization) were placed in an 8-mL autoclave vial containing a PTFE-coated stirring bar. The autoclave vial was closed using a screw cap with septum and flushed with argon (10 min). Hexafluoroisopropanol (HFIP, 4 mL) and $BF_3$*$OEt_2$ (1 mol % with respect to 1-(2,2,4-trimethyl-1-quinolyl)ethanone) were added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the

TABLE 5

| Example | Additive (mol %) | Scale (amount of compound (II)) | Reaction time (h) | catalyst loading (mol %) | Conversion GC (% a/a) | Enantiomeric excess (% ee) |
|---|---|---|---|---|---|---|
| 49 | — | 9 mmol | 6 | 0.01 | 50.8 | n.d. |
| 50 | $B(C_6F_5)_3$ (0.5) | 9 mmol | 20 | 0.01 | 85.2 | n.d. |
| 51 | $BF_3$*$OEt_2$ (1) | 10 mmol | 16 | 0.01 | 99.2 | n.d. |
| 52 | $Al(OTf)_3$ (1) | 10 mmol | 16 | 0.01 | >99 | n.d. |
| 53 | $HPF_6$ (1) | 9 mmol | 16 | 0.01 | 97.3 | n.d. |
| 54 | $BF_3$*AcOH (1) | 9 mmol | 16 | 0.01 | 98.1 | n.d. |

Examples 55-56

The Ir-complex (identifier and catalyst loading given) and 0.64 g 1-(2,2,4-trimethyl-1-quinolyl)ethanone (3 mmol, vial was taken out of the autoclave and the reactions outcome was determined by GC-FID analysis (deluted with EtOH) and the enantiomeric excess by HPLC analysis. Typical values are given.

TABLE 6

| Example | Catalyst | Additive (mol %) | Reaction time (h) | catalyst loading (mol %) | Conversion GC (% a/a) | Enantiomeric excess (% ee) |
|---|---|---|---|---|---|---|
| 55 | Va-6 | — | 3 | 0.02 | 78.8 | 98.8 |
| 56 | Va-6 | $BF_3$*$OEt_2$ (1) | 3 | 0.02 | 94.2 | 99 |

Examples 57-60

The Ir-complex Va-1 (0.02 mol %, 0.6 mol) and 0.64 g 1-(2,2,4-trimethyl-1-quinolyl)ethanone (3 mmol, purified with heptane: water wash+crystallization) were placed in an 8-mL autoclave vial containing a PTFE-coated stirring bar. The autoclave vial was closed using a screw cap with septum and flushed with argon (10 min). 2,2,2-Trifluoroethanol (TFE, 4 mL) and $BF_3*OEt_2$ (loading given) were added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for 3 h. After cooling to room temperature and depressurizing, the vial was taken out of the autoclave and the reactions outcome was determined by GC-FID analysis (deluted with EtOH) and the enantiomeric excess by HPLC analysis. Typical values are given.

TABLE 7

| Example | $BF_3*OEt_2$ (mol %) | Conversion GC (% a/a) |
|---|---|---|
| 57 | — | <1 |
| 58 | 1 | 86 |
| 59 | 3 | 88 |
| 60 | 5 | 82 |

Comparative Examples

The Ir-complex (catalyst loading given) and 0.64 g 1-(2,2,4-trimethyl-1-quinolyl)ethanone (3 mmol) were placed in an 8-mL autoclave vial containing a PTFE-coated stirring bar. The autoclave vial was closed using a screw cap with septum and flushed with argon (10 min). Hexafluoroisopropanol (HFIP, 4 mL) was added via the septum to the vial. The vial was placed in an argon containing autoclave and the autoclave was flushed with argon (10 min). The autoclave was pressurized with hydrogen gas (10 bar) and subsequently depressurized to atmospheric pressure three times. After this the autoclave was pressurized to 60 bar hydrogen pressure and was placed in a suitable alumina block. After heating to 85° C. the reaction was kept at this temperature for the given time. After cooling to room temperature and depressurizing, the vial was taken out of the autoclave and the reactions outcome was determined by GC-FID analysis (deluted with EtOH) and the enantiomeric excess by HPLC analysis.

TABLE 8

| Example | Catalyst | Catalyst loading (mol %) | Time (h) | Conversion |
|---|---|---|---|---|
| 17 | Va-1 | 0.01 | 6 | 50.8 |
| 18 | Va-2 | 0.01 | 6 | 53.4 |
| 15 | Va-1 | 0.01 | 17 | 93.1 |
| 13 | Va-10 | 0.01 | 17 | 82.5 |
| 61 | Va-10 | 0.025 | 16.5 | 98 |
| 62 | Va-13 | 0.1 | 16 | 99.2 |
| 63 | Ir catalyst (1) | 0.1 | 16 | 84 |

This collection of experimental results shows the superiority of complexes Va-1 and Va-2. Va-2 performs gives slightly higher conversion than Va-1 after 6 h with 0.01 mol % of catalyst. Va-1 gives significantly higher conversion than Va-10 (=Va-10 from WO2019/185541 A1) after 17 h with 0.01 mol % of catalyst. Va-10 gives similar performance than Va-13 (=Va-1 from WO2019/185541 A1) although only ¼ of the catalyst amount was used. It must thus be considered superior to Va-13. Va-13 gives superior conversion compared to Ir catalyst (I) from DE112015001290 T5. Moreover, all of the catalyst Va gives superior enantioslectivities (>95% ee) compared to Ir catalyst (1) from DE112015001290 T5 (81.7% ee). Catalyst Va-1 gives higher conversion (93.1 vs 84%) than Ir catalyst (1) from DE112015001290 T5 even at only one-tenths ofthe catalyst loading (0.01 vs 0.1 mol %).

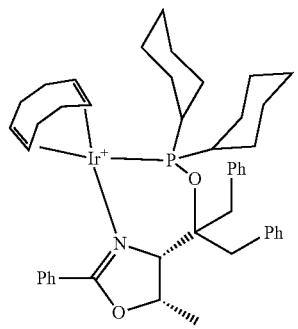

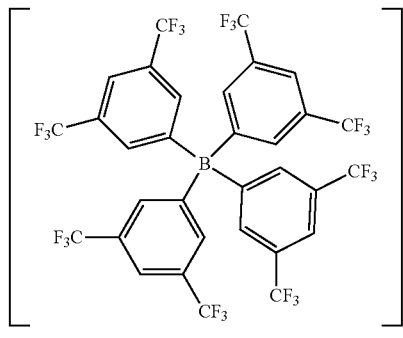

Ir catalyst (1) from DE112015001290T5

The invention claimed is:

1. A process for preparing a compound of formula (Ia) or (Ib),

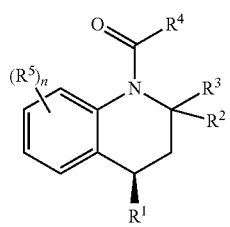

(Ia)

-continued (Ib)

wherein
R¹ is selected from the group consisting of $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_6$-$C_{14}$-aryl, or $C_6$-$C_{14}$-aryl-$C_1$-$C_4$-alkyl,
wherein the $C_1$-$C_6$-alkyl, $C_3$-$C_6$-cycloalkyl and the $C_1$-$C_6$-alkoxy in the $C_1$-$C_6$-alkoxy-$C_1$-$C_6$-alkyl moiety, are optionally substituted by 1 to 3 substituents independently selected from the group consisting of halogen, $C_1$-$C_4$-alkoxy, $C_1$-$C_4$-haloalkyl, $C_1$-$C_4$-haloalkoxy and phenyl, wherein the phenyl may be substituted by one to five substituents selected independently from each other from halogen, $C_1$-$C_4$-alkyl, $C_1$-$C_4$-alkoxy, $C_1$-$C_4$-haloalkyl, and $C_1$-$C_4$-haloalkoxy, and
wherein the $C_6$-$C_{14}$-aryl and the $C_6$-$C_{14}$-aryl in the $C_6$-$C_{14}$-aryl-$C_1$-$C_4$-alkyl moiety in each case is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy,
R² and R³ are the same and are selected from the group consisting of hydrogen, $C_1$-$C_6$-alkyl, $C_1$-$C_6$-haloalkyl and $C_1$-$C_6$-alkoxy-$C_1$-$C_6$-alkyl,
or
R² and R³ together with the carbon which they are bound to, form a $C_3$-$C_6$-cycloalkyl ring,
R⁴ is hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_2$-$C_6$-alkenyloxy, 9-flurorenylmethyleneoxy, $C_6$-$C_{14}$-aryl, $C_6$-$C_{14}$-aryloxy, $C_6$-$C_{14}$-aryl-$C_1$-$C_4$-alkyloxy or $C_6$-$C_{14}$-aryl-$C_1$-$C_4$-alkyl,
wherein the $C_6$-$C_{14}$-aryl as such or as part of a composite substituent is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy,
n is 0, 1, 2, 3 or 4,
each substituent R⁵, if present, is independently selected from the group consisting of halogen, $C_1$-$C_6$-alkyl, $C_1$-$C_6$-haloalkyl, $C_1$-$C_6$-alkoxy, hydroxyl, amino and —C(=O)—$C_1$-$C_6$-alkyl,
the process comprising enantioselective hydrogenation of a compound of formula (II)

(II)

wherein the substituents R¹, R², R³, R⁴, R⁵ and the integer n are each as defined for the compound of formula (Ia) or (Ib),
in presence of a chiral iridium catalyst,
wherein the chiral iridium catalyst is of the general formula (Va) or (Vb)

(Va)

(Vb)

wherein
R⁶ is 2,6-diethyl-4-methylphenyl,
R⁷ is hydrogen,
R⁸ is methyl,
R⁹ and R¹⁰ are both cyclohexyl,
Y is a non-coordinating anion selected from the group consisting of $[B(R^{18})_4]^-$ and $[Al\{OC(CF_3)_3\}_4]^-$ of formula (VII), (VII)

wherein R¹⁸ is 3,5-bis(trifluoromethyl)phenyl.

2. The process according to claim 1, wherein
R¹ is $C_1$-$C_6$-alkyl or $C_6$-$C_{14}$-aryl-$C_1$-$C_4$-alkyl,
wherein $C_6$-$C_{14}$-aryl in the $C_6$-$C_{14}$-aryl-$C_1$-$C_4$-alkyl moiety is unsubstituted or substituted by one to five substituents selected from the group consisting of halogen, $C_1$-$C_4$-alkyl, $C_1$-$C_4$-haloalkyl, $C_1$-$C_4$-alkoxy and $C_1$-$C_4$-haloalkoxy,
R² and R³ are the same and are selected from $C_1$-$C_4$-alkyl,
R⁴ is $C_1$-$C_4$-alkyl, $C_1$-$C_4$-haloalkyl, $C_1$-$C_4$-alkoxy, $C_1$-$C_4$-haloalkoxy, phenyl or benzyl,
n is 0, 1 or 2, each substituent $R^5$, if present, is independently selected from the group consisting of halogen, $C_1$-$C_6$-alkyl and $C_1$-$C_6$-haloalkyl.

3. The process according to claim 1, wherein
$R^1$ is $C_1$-$C_6$-alkyl,
$R^2$ and $R^3$ are the same and are selected from $C_1$-$C_4$-alkyl,
$R^4$ is $C_1$-$C_4$-alkyl, $C_1$-$C_4$-haloalkyl, $C_1$-$C_4$-alkoxy, $C_1$-$C_4$-haloalkoxy, phenyl or benzyl,
n is 0, 1 or 2,
each substituent $R^5$, if present, is independently selected from the group consisting of halogen, $C_1$-$C_6$-alkyl and $C_1$-$C_6$-haloalkyl.

4. The process according to claim 1, wherein
$R^1$ is $C_1$-$C_6$-alkyl,
$R^2$ and $R^3$ are the same and are selected from $C_1$-$C_4$-alkyl, or
$R^2$ and $R^3$ together with the carbon which they are bound to, form a $C_3$-$C_6$-cycloalkyl ring,
$R^4$ is $C_1$-$C_4$-alkyl, $C_1$-$C_4$-haloalkyl, phenyl or benzyl,
n is 0, 1 or 2,
each substituent $R^5$, if present, is independently selected from the group consisting of halogen and $C_1$-$C_6$-alkyl.

5. The process according to claim 1, wherein
$R^1$ is $C_1$-$C_4$-alkyl,
$R^2$ and $R^3$ are methyl,
$R^4$ is $C_1$-$C_4$-alkyl,
n is 0 or 1,
$R^5$ if present, is fluorine.

6. The process according to claim 1, wherein the process is performed in presence of an additive, which is selected from the group consisting of Bronsted acids, Lewis acids, and mixtures thereof.

7. The process according to claim 6, wherein the additive is selected from the group consisting of hexafluorophosphoric acid, pentafluorophenol, 3,5-bis(trifluoromethyl)phenol, triphenylborane, tris[3,5-bis(trifluoro-methyl)phenyl]borane, tris(2,3,4,5,6-pentafluorophenyl)borane, aluminum (III) trifluoromethanesulfonate, scandium (III) trifluoromethanesulfonate, aluminum (III) fluoride, titanium (IV) isopropoxide, trimethyl aluminum, boron trifluoride, complexes of boron trifluoride, and mixtures thereof.

8. The process according to claim 1, wherein the hydrogenation is conducted using hydrogen gas at a pressure of from 1 to 300 bar.

9. The process according to claim 1, wherein the amount of chiral iridium catalyst used is within the range of from 0.001 mol % to 5 mol %, based on the amount of the compound of formula (II).

10. The process according to claim 1, wherein the hydrogenation is conducted at a temperature within the range of from 20° C. to 130° C.

11. The process according to claim 1, wherein the amount of additive used is within the range of from 0.1 mol % to 10 mol %.

12. A chiral iridium catalyst selected from chiral iridium catalysts of general formulae (Va) and (Vb)

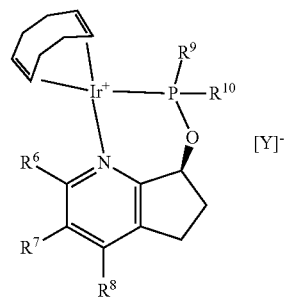
(Va)

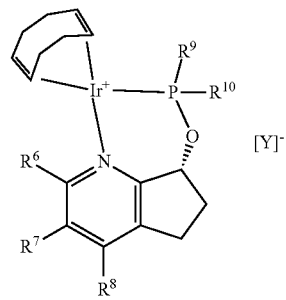
(Vb)

wherein
$R^6$ is 2,6-diethyl-4-methylphenyl,
$R^7$ is hydrogen,
$R^8$ is methyl,
$R^9$ and $R^{10}$ are both cyclohexyl,
Y is a non-coordinating anion selected from the group consisting of $[B(R^{18})_4]^-$ and $[Al\{OC(CF_3)_3\}_4]^-$ of formula (VII),

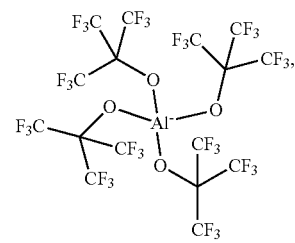
(VII)

wherein $R^{18}$ is 3,5-bis(trifluoromethyl)phenyl.

13. The chiral iridium catalyst according to claim 12, wherein the chiral iridium catalyst is the chiral iridium catalyst of formula (Va)

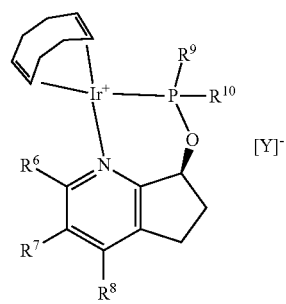
(Va)

wherein
$R^6$ is 2,6-diethyl-4-methylphenyl,
$R^7$ is hydrogen,
$R^8$ is methyl,
$R^9$ and $R^{10}$ are both cyclohexyl,
Y is the non-coordinating anion $[B(R^{18})_4]^-$,
   wherein $R^{18}$ is 3,5-bis(trifluoromethyl)phenyl.

14. The chiral iridium catalyst according to claim 12, wherein the chiral iridium catalyst is the chiral iridium catalyst of formula (Va)

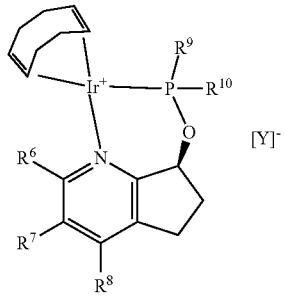

(Va)

wherein
$R^6$ is 2,6-diethyl-4-methylphenyl,
$R^7$ is hydrogen,
$R^8$ is methyl,
$R^9$ and $R^{10}$ are both cyclohexyl,
Y is the non-coordinating anion $[Al\{OC(CF_3)_3\}_4]^-$ of formula (VII)

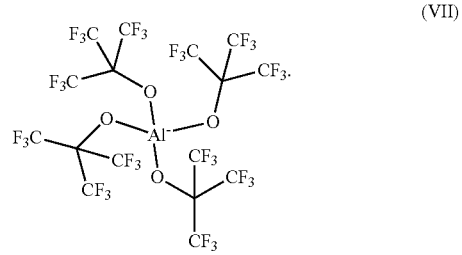

(VII)

* * * * *

UNITED STATES PATENT AND TRADEMARK OFFICE
CERTIFICATE OF CORRECTION

PATENT NO. : 12,410,138 B2
APPLICATION NO. : 17/640287
DATED : September 9, 2025
INVENTOR(S) : Schotes et al.

Page 1 of 2

It is certified that error appears in the above-identified patent and that said Letters Patent is hereby corrected as shown below:

On the Title Page

In Item (56), under "OTHER PUBLICATIONS", in Column 2, Line 10, delete "Blcok,"" and insert -- Block," --, therefor.

On Page 2, in Item (56), under "OTHER PUBLICATIONS", in Column 1, Line 5, delete "iridiumeP∧N" and insert -- iridiumP^N --, therefor.

In the Specification

In Column 1, Line 47, delete "asymmetic" and insert -- asymmetric --, therefor.

In Column 2, Line 2, delete "(Ta) or (Tb)," and insert -- (Ia) or (Ib), --, therefor.

In Column 3, Line 17, delete "(Ta) or (Tb)," and insert -- (Ia) or (Ib), --, therefor.

In Column 4, Lines 2-3, delete "$C_3$-$C_5$-cycloalkyl," and insert -- $C_3$-$C_8$-cycloalkyl, --, therefor.

In Column 7, Line 37, delete "und" and insert -- and --, therefor.

In Column 7, Line 56, delete "(Ta) or (Tb)," and insert -- (Ia) or (Ib), --, therefor.

In Column 8, Line 42, delete "R," and insert -- $R^3$, --, therefor.

In Column 8, Line 45, delete "(Ta) or (Tb)." and insert -- (Ia) or (Ib). --, therefor.

In Column 10, Lines 45-46, delete "[Al{OC(CF$_3$)3}$_4$]$^-$" and insert -- [Al{OC(CF$_3$)$_3$}$_4$]$^-$ --, therefor.

Signed and Sealed this
Ninth Day of December, 2025

John A. Squires
*Director of the United States Patent and Trademark Office*

CERTIFICATE OF CORRECTION (continued)
U.S. Pat. No. 12,410,138 B2

In Column 11, Line 46, delete "[Al{OC(CF$_3$)3}$_4$]$^-$" and insert -- [Al{OC(CF$_3$)$_3$}$_4$]$^-$ --, therefor.

In Column 12, Lines 30-31, delete "trifluoromethylsulfonic" and insert -- trifluoromethanesulfonic --, therefor.

In Column 15, Line 47, delete "C40H58NOPIr" and insert -- C$_{40}$H$_{58}$NOPIr --, therefor.

In Column 15, Line 63, delete "Li{A1[OC(CF$_3$)$_3$]$_4$}" and insert -- Li{Al[OC(CF$_3$)$_3$]$_4$} --, therefor.

In Column 18, Line 13, delete "Li{A1[OC(CF$_3$)$_3$]$_4$}" and insert -- Li{Al[OC(CF$_3$)$_3$]$_4$} --, therefor.

In Column 18, Lines 26-29, delete "The reaction....... [Ir(COD)$_2$]BARF)." and insert the same at Line 27, as a new paragraph.

In Column 19, Line 30, delete "(deluted" and insert -- (diluted --, therefor.

In Column 20, Line 12, delete "(deluted" and insert -- (diluted --, therefor.

In Column 20, Line 38, delete "mi)." and insert -- min). --, therefor.

In Column 20, Line 51, delete "(deluted" and insert -- (diluted --, therefor.

In Column 21, Line 27, delete "Jr-complex" and insert -- Ir-complex --, therefor.

In Column 21, Line 40, delete "(deluted" and insert -- (diluted --, therefor.

In Column 22, Line 56, delete "(deluted" and insert -- (diluted --, therefor.

In Column 23, Line 3, delete "mol)" and insert -- µmol) --, therefor.

In Column 23, Line 20, delete "(deluted" and insert -- (diluted --, therefor.

In Column 23, Line 51, delete "(deluted" and insert -- (diluted --, therefor.